(12) United States Patent
Sauer

(10) Patent No.: US 10,231,729 B2
(45) Date of Patent: Mar. 19, 2019

(54) FERRULE HOLDER WITH SUTURE RELIEF LOBES

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 76 days.

(21) Appl. No.: 15/388,608

(22) Filed: Dec. 22, 2016

(65) Prior Publication Data

US 2017/0100120 A1    Apr. 13, 2017

Related U.S. Application Data

(63) Continuation of application No. 12/039,503, filed on Feb. 28, 2008.

(51) Int. Cl.
*A61B 17/04* (2006.01)
*A61B 17/06* (2006.01)

(52) U.S. Cl.
CPC ...... *A61B 17/0482* (2013.01); *A61B 17/0469* (2013.01); *A61B 17/0483* (2013.01); *A61B 17/0491* (2013.01); *A61B 17/06061* (2013.01)

(58) Field of Classification Search
CPC ............ A61B 17/0469; A61B 17/0482; A61B 17/0483; A61B 17/06061
See application file for complete search history.

(56) References Cited

U.S. PATENT DOCUMENTS

| 5,318,577 | A  | * | 6/1994  | Li ...................... A61B 17/0469 606/147 |
| 5,391,174 | A  |   | 2/1995  | Weston |
| 5,792,153 | A  | * | 8/1998  | Swain ................. A61B 17/0469 112/169 |
| 6,443,963 | B1 | * | 9/2002  | Baldwin ............. A61B 17/0482 606/139 |
| 6,533,795 | B1 |   | 3/2003  | Tran |
| 6,533,796 | B1 |   | 3/2003  | Sauer |
| 6,551,330 | B1 | * | 4/2003  | Bain .................. A61B 17/0469 606/144 |
| 6,770,084 | B1 | * | 8/2004  | Bain .................. A61B 17/0469 606/144 |
| 6,893,448 | B2 |   | 5/2005  | O'Quinn |
| 2003/0181924 | A1 | * | 9/2003 | Yamamoto ......... A61B 17/0467 606/144 |
| 2003/0208209 | A1 | * | 11/2003 | Gambale .......... A61B 17/00234 606/144 |
| 2004/0097968 | A1 |  | 5/2004 | Shikhman |

(Continued)

OTHER PUBLICATIONS

Dec. 10, 2009 International Search Report; PCT—Written Opinion of the International Searching Authority in International Application No. PCT/US2009/035080.

(Continued)

*Primary Examiner* — Alexander J Orkin
(74) *Attorney, Agent, or Firm* — Christopher B. Miller

(57) ABSTRACT

A surgical suturing instrument has a chamber for receiving and aligning a ferrule with a reciprocating needle. The chamber includes a plurality of protuberant concave and convex surfaces for positioning and aligning the ferrule within the chamber and the plurality of suture receiving chambers disposed between the aligning ridges for receiving a suture and preventing the suture from jamming the ferrule in the chamber.

4 Claims, 4 Drawing Sheets

(56) References Cited

U.S. PATENT DOCUMENTS

2005/0154403 A1     7/2005   Sauer
2005/0228407 A1    10/2005   Nobles

OTHER PUBLICATIONS

Apr. 29, 2011; Office Action in U.S. Appl. No. 12/039,503.
Jul. 29, 2011 Response to Office Action in U.S. Appl. No. 12/039,503.
Nov. 28, 2011; Office Action in U.S. Appl. No. 12/039,503.
Jan. 27, 2012 Response to Office Action in U.S. Appl. No. 12/039,503.
Mar. 29, 2013; Office Action in U.S. Appl. No. 12/039,503.
Jun. 28, 2013 Response to Office Action in U.S. Appl. No. 12/039,503.
Sep. 27, 2013; Office Action in U.S. Appl. No. 12/039,503.
Mar. 24, 2014 Appeal Brief in U.S. Appl. No. 12/039,503.
Apr. 24, 2014; Mashack, Mark F. Examiner's Answer in U.S. Appl. No. 12/039,503.
Jun. 25, 2014 Reply Brief in U.S. Appl. No. 12/039,503.
Nov. 22, 2014 : PTAB: Decision on Appeal in U.S. Appl. No. 12/039,503.

\* cited by examiner

FERRULE HOLDER WITH SUTURE RELIEF LOBES

FIELD

The present invention relates generally to improvements in the ferrule receiving tips used on surgical suturing instruments of the type generally shown in U.S. patent application Ser. No. 10/845,040 and related patents.

BACKGROUND

The instruments to which the claimed invention is addressed offer many novel features that improve a surgeon's ability to place multiple suture bites for running sutures during minimally invasive surgery. This new enhancement addresses an infrequent, but significant problem of suture jamming between a ferrule and the ferrule holder, which was noted after introduction of this product for actual use in the operating room.

During device rearming (i.e., re-insertion of the ferrule into its compartment after passing through a section of tissue), on occasion surgeons were not always properly orienting the suture relative to the device tip. This improper suture orientation can cause the suture to be positioned in the ferrule compartment in a way that causes irreversible jamming of the suture and ferrule within the ferrule compartment. To overcome the problem of suture jamming in the ferrule compartment in the distal tip during rearming, this novel enhancement provides adequate clearance spaces around the ferrule to receive an improperly oriented suture, while still precisely holding the ferrule in its targeted location.

SUMMARY

To use the surgical suturing device for placement of suture, the operator squeezes a lever which drives a single faceted needle forward. The needle traverses through tissue placed in a gap in the distal jaw of the device and then into an open end of a ferrule attached to one end of a suture. For the needle to enter and engage the ferrule, the ferrule must be aligned in the needle's pathway in the distal tip of the jaw. Upon release of the lever, the needle retracts back pulling the now engaged ferrule with suture past a latch in the distal tip and through the tissue. Automated rotation of the needle controls whether the distal tip latch releases or retains (strips off) the ferrule within the ferrule compartment.

To rearm the device prior to placing another bite for a running stitch, the lever is squeezed again to advance the needle still attached to the ferrule and suture through the now empty gap in the device jaw. A suture slot is provided in the ferrule slot so that the suture may pass through this slot during reinstallation of the ferrule with suture back into the ferrule compartment. Surgeons are taught to orient the device tip and its suture slot with the suture to ensure proper suture orientation for rearming. Without the present claimed invention with its clearance grooves, as in the previously manufactured substantially round ferrule compartment with a slot for receiving a suture, a suture not properly oriented to pass through the suture slot can result in the suture becoming jammed between the ferrule and the wall of its round compartment during ferrule rearming. Without this new feature, not only is the suture typically damaged or broken, but more significantly, the ferrule often becomes so tightly held within the compartment by the now compressed suture, that the needle is unable to pull the ferrule back out of its compartment for the next tissue bite.

The claimed invention works by providing additional clearance space or spaces in the shape of longitudinally oriented grooves or chambers in the ferrule compartment. The ferrule is still held aligned in place along three contact areas radially spaced around the inner periphery of the ferrule receiving compartment for adequate needle tip targeting. In place of the original round, snug suture compartment, devices in accordance with this invention have two longitudinally oriented suture receiving chambers or grooves in addition to the suture slot. In this preferred embodiment, this ferrule compartment configuration, typically called a tri-lobe clearance feature, is readily manufacturable and has proven remarkably effective during many surgical procedures.

Despite training, it was found during actual surgical use, surgeons with some regularity do not properly orient suture as taught during rearming. Without this means of removal of the ferrule after suture jamming, the entire device is typically rendered unusable. Depending on suture type being used, with this new feature, failure to properly orient the suture now may cause no noticeable problem (with more flexible braided suture), or just suture damage or breakage (with less flexible monofilament suture), but the device is salvageable because the ferrule remains steadily removable from its compartment. Removal of the ferrule from the needle permits reloading of the system for another running suture.

BRIEF DESCRIPTION OF THE DRAWING FIGURES

DETAILED DESCRIPTION

Figure 1A:
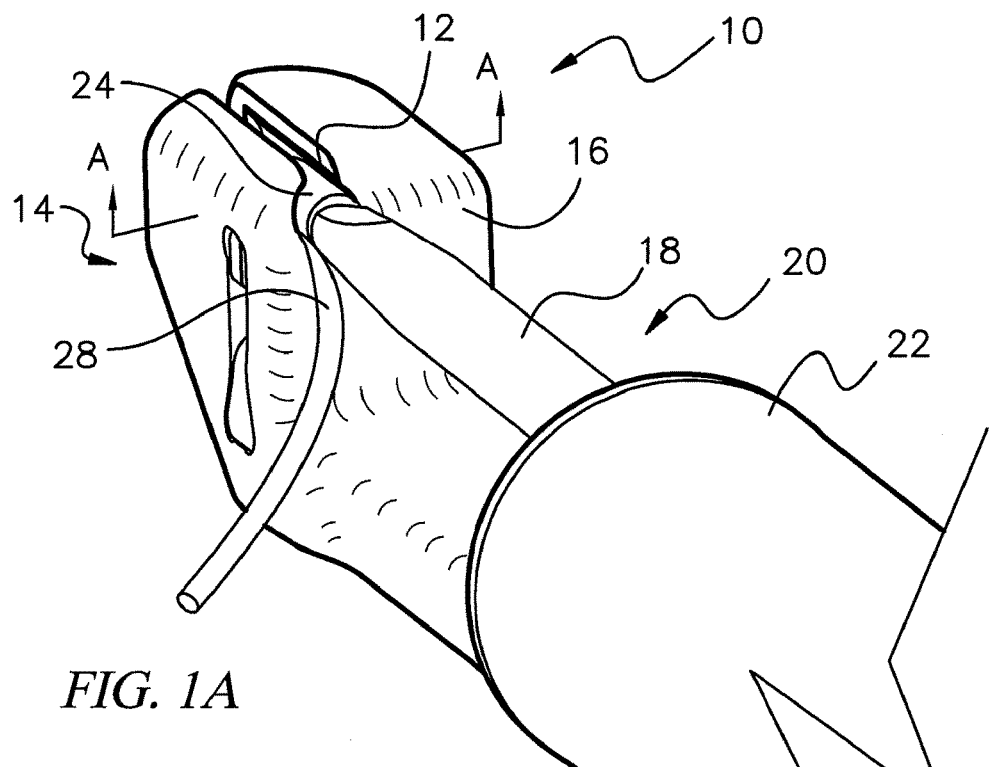
FIGS. 1A and 1B are a perspective view and a cross-section view respectively of a surgical suturing instrument having a ferrule compartment in accordance with the prior art.
Figure 1B:
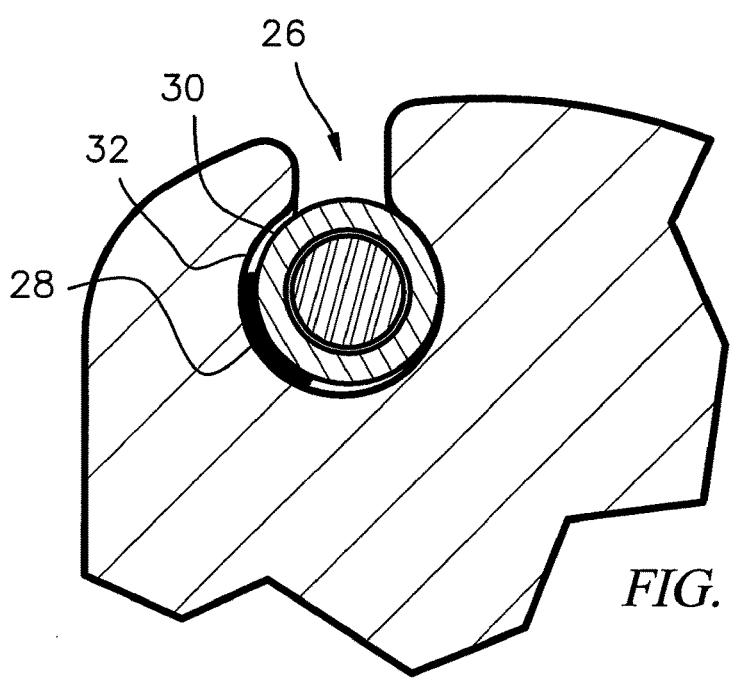

FIGS. 1A and 1B are a perspective view and a section view (taken along line A-A) of the distal end of a surgical suturing instrument 10 employing a ferrule receiving compartment 12 in accordance with the prior art. The surgical instrument indicated generally at 10 includes a tip indicated generally at 14 having a ferrule receiving compartment disposed in an inwardly facing surface 16 thereof. A needle 18 that is movable reciprocally across a gap 20 between the tip 14 and the body 22 of the surgical suturing instrument is shown engaged with a ferrule 24 disposed in the compartment 12 in FIGS. 1A and 1B. The ferrule receiving compartment 12 includes a generally upwardly (as shown in the figure) opening slot 26 that is designed to accommodate the portion of the suture 28 proximate to the ferrule. As long as the suture is positioned within the upwardly opening slot, the ferrule may be readily inserted into and removed from the compartment by the reciprocating end of the needle, which holds the ferrule by fractional forces. However, if, as shown in FIGS. 1A and 1B, the suture becomes wedged between the outside surface 30 of the ferrule 24 and the inside round surface 32 of the ferrule receiving compartment, the ferrule may become jammed in the compartment and incapable of being easily removed from the round ferrule compartment. When this happens, the instrument becomes temporarily un-useable until the ferrule is released from the compartment, which almost always requires withdrawal of the instrument from the operating site and the use of additional tools to aid in the ferrule extraction. It will be appreciated that if this occurs during the placement of the running stitch, it may be necessary to cut the suture and replace the stitch.

Figure 2A:
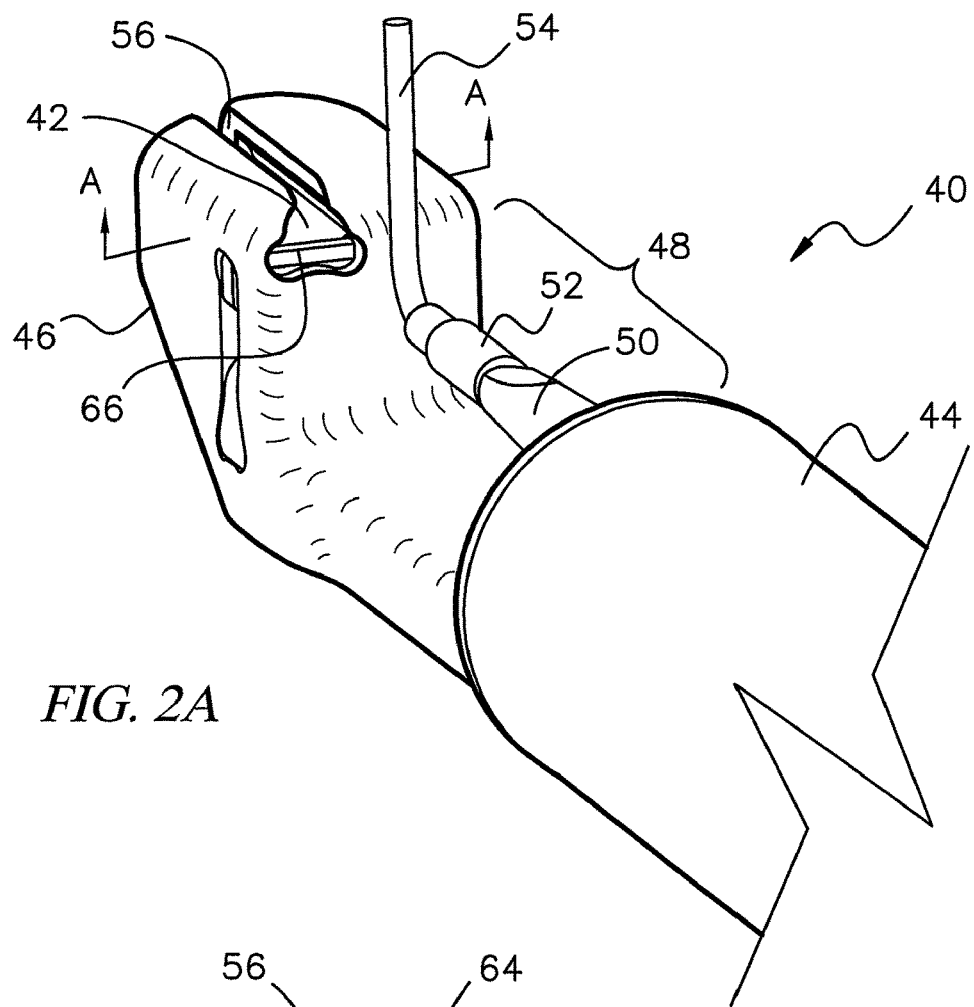
FIGS. 2A and 2B are a perspective view and a sectional view respectively of a surgical suturing instrument in accordance with this invention in a first position.

FIG. 2A is a perspective view of the distal end of a surgical suturing implement 40 having a specialized ferrule receiving chamber 42 in accordance with this invention. The instrument indicated generally at 40 includes an elongated body 44, only the distal portion of which is shown, terminating in a tip 46 having a recess or gap 48 across the upper portion of which a needle 50 reciprocates into and out of engagement with a ferrule receiving compartment 42 formed on the distal side of the gap. As shown in FIG. 2A, a ferrule 52 is frictionally engaged with the tip of the needle 50 and a length of suture 54 extends from the end of the ferrule opposite the needle engaging end.

The ferrule receiving compartment 42 includes a slot 56 opening upwardly as shown in the drawing, through which the suture 54 can readily pass when oriented as shown in FIG. 2A. The ferrule receiving compartment also includes three spaced apart surfaces 60, 62, 64 that can contact an outside surface of the ferrule 52 to align the ferrule in the ferrule compartment. A moveable latch 66 is disposed in the lower part of the compartment for engaging the ferrule and retaining it in the compartment to strip it from the needle when it is desired to detach the needle from the ferrule. This permits the instrument to be used to create a running stitch as shown in U.S. patent application Ser. No. 10/845,040. While a metal ferrule of a type commonly used in instruments of the type to which this claimed invention is addressed is illustrated and described herein, the claimed invention is not limited to any particular type of ferrule. For example, ferrules made from other materials, or sutures having ends configured to selectively receive and release a needle for pulling the suture through a tissue section may also be used. As used here in ferrule is intended to include any structure that allows a needle to be selectively coupled to the end of a suture.

Figure 2B:
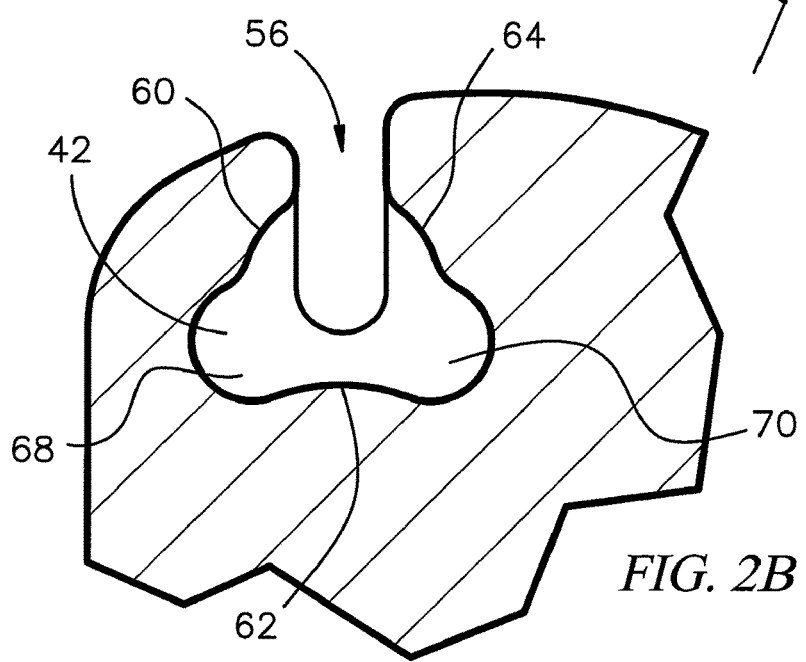

FIG. 2B is a cross section taken along line A-A of FIG. 2A showing the shape of the periphery of the ferrule compartment. In this preferred embodiment, an upper portion of the chamber is bisected by an upwardly oriented open slot 56 permitting the suture to pass there through when the ferrule is first withdrawn from the slot during the placement of a stitch. The slot is disposed between first and second adjacent concave surfaces 60, 64 providing separated ferrule aligning surfaces in the compartment. A convex topped surface 62 is located opposite surfaces 60 and 64. The compartment also includes first and second suture receiving clearance chambers 68, 70 disposed between the first and second 60, 62, and second and third 62, 64 ferrule engaging surfaces. These clearance chambers are contoured such that a suture not oriented to exit through the suture slot 56 will naturally shift into one of these clearance chambers following a path of least resistance. In addition, these chambers provide a space for the suture to pass freely without jamming.

The chamber also includes a releasable latching bar 66 for engaging the ferrule for selectively retaining the ferrule in the compartment or releasing the ferrule to be carried through a tissue section by the needle tip.

FIG. 2B is a cross section taken along line A-A of FIG. 2 showing the shape of the periphery of the ferrule compartment and the location of the concave surfaces and convex topped surfaces.

Figure 3A:
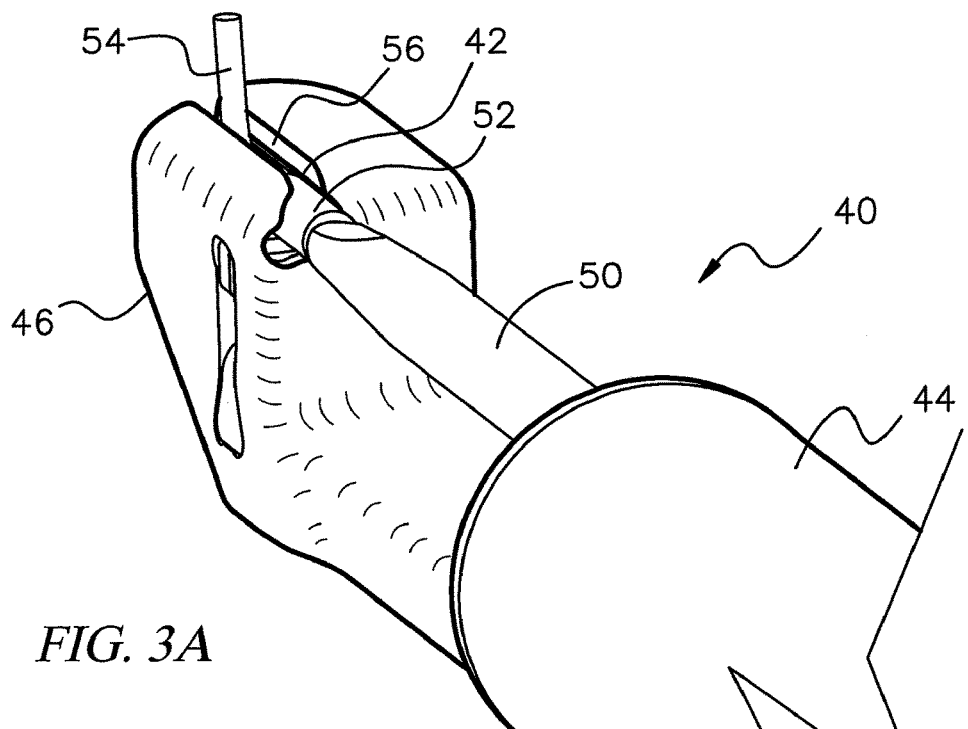
FIGS. 3A and 3B are a perspective view and a sectional view respectively of a surgical suturing instrument in accordance with this invention in a second position with the suture oriented properly exiting the suture slot.
Figure 3B:
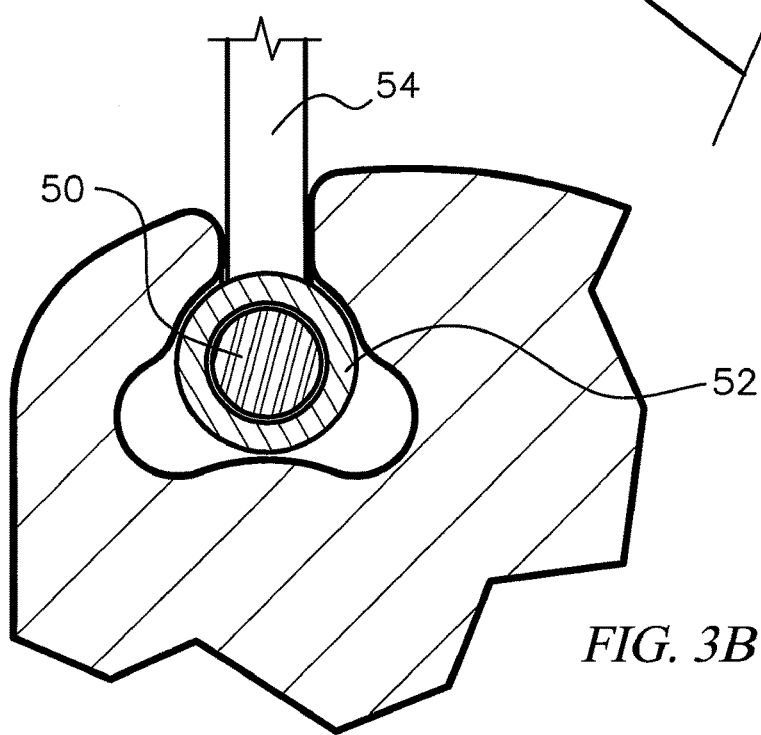

FIG. 3A is another perspective view of the tip of a surgical suturing instrument in accordance with this invention showing the reciprocating needle 50 extended towards the distal end of the instrument 40 and the ferrule 52 disposed within the ferrule receiving compartment 42. FIGS. 3A and 3B show the suture positioned within the upwardly opening suture receiving slot 56. The suture 54 can move proximally and distally within slot freely without binding.

Figure 4A:
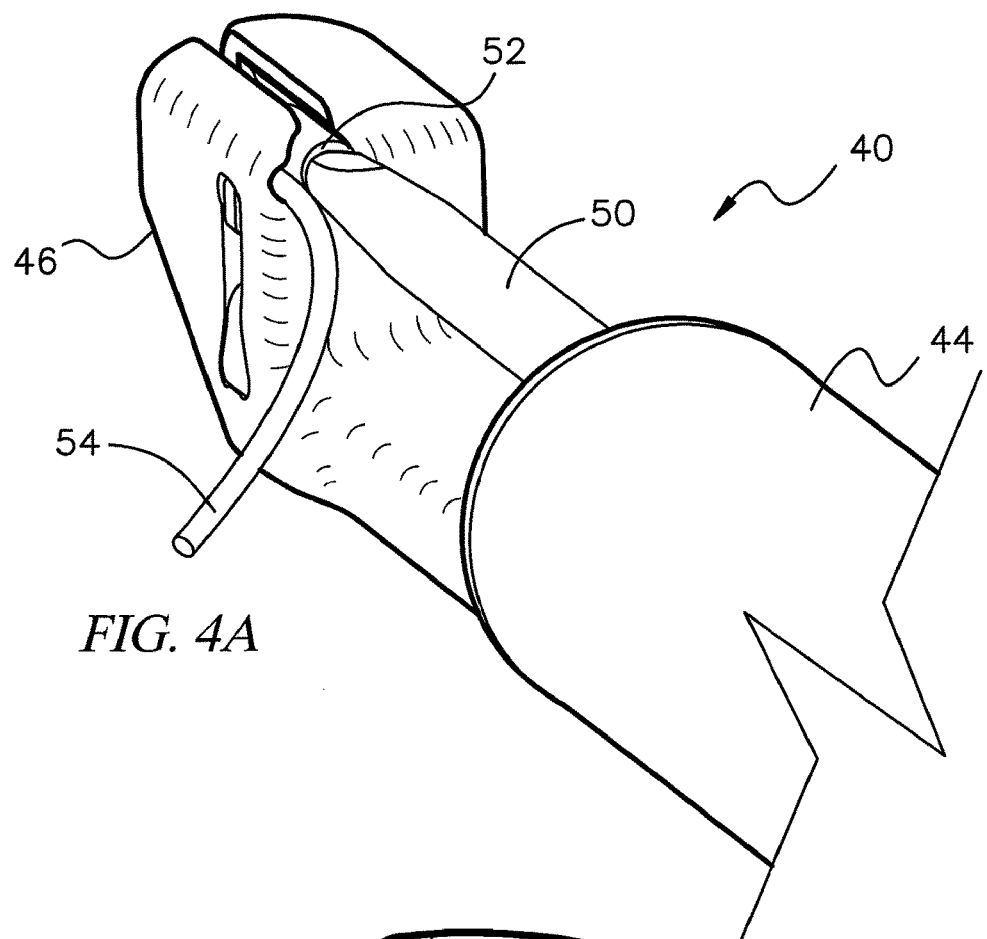
FIGS. 4A and 4B are a perspective view and a sectional view respectively of a surgical suturing instrument in accordance with this invention also in a second position but now with the suture exiting through one of the tri-lobe clearance features.
Figure 4B:
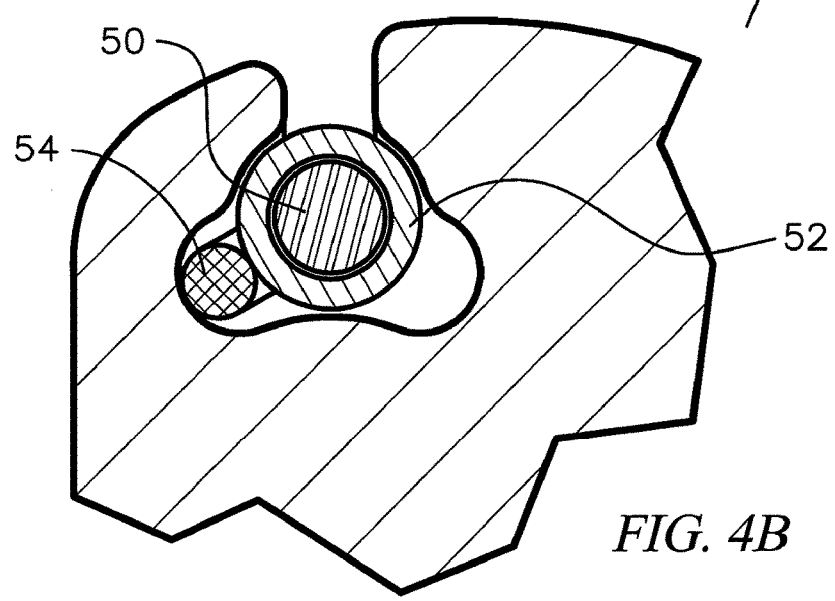

FIG. 4A shows the same instrument as shown in FIG. 2A but with the suture 54 led proximally from the distal end of the ferrule 52 through the suture receiving chamber 68. It will be readily appreciated from FIGS. 4A and 4B that the claimed invention permits the suture to be positioned more freely with respect to the ferrule without jamming the ferrule in the ferrule receiving compartment as was possible with the prior art construction shown in FIGS. 1A and 1B.

While the invention has been shown in connection with a presently preferred embodiment thereof, those skilled in the art will recognize that certain modifications and changes may be made therein without departing from the true spirit and scope of the invention which accordingly is intended to be defined solely by the appended claims.

What is claimed is:

1. A surgical suturing implement, comprising:
    a) an elongated body;
    b) a distal tip coupled to the elongated body, the tip defining:
        1) a tissue gap across an upper portion; and
        2) a ferrule receiving compartment having:
            i) a ferrule receiving opening having three spaced apart surfaces for contacting an outside surface of a ferrule and aligning the ferrule within the opening;
            ii) a suture receiving slot disposed between first and second adjacent ones of the three spaced apart surfaces;
            iii) a first suture receiving chamber disposed between first and third adjacent ones of the three spaced apart surfaces; and
            iv) a second suture receiving chamber disposed between second and third adjacent ones of the three spaced apart surfaces; and
    c) a needle moveable within the elongated body and across the tissue gap in the distal tip to alignment within the ferrule receiving opening, but not within the first or second suture receiving chambers.

2. The surgical suturing instrument of claim 1, wherein the three spaced apart surfaces comprise concave and convex surfaces.

3. The surgical suturing instrument of claim 2, in which two of the spaced apart surfaces are concave surfaces and the third spaced apart surface is a convex surface.

4. The surgical suturing instrument of claim 1, further comprising a moveable latch and wherein the distal tip further defines a compartment for the moveable latch such that the movable latch is movable through the first and second suture receiving chambers and into the ferrule receiving opening.

\* \* \* \* \*